(12) United States Patent
Risse et al.

(10) Patent No.: US 8,338,631 B2
(45) Date of Patent: Dec. 25, 2012

(54) PROCESS FOR PREPARING DIALKYL CARBONATES FROM ALKYLENE CARBONATES AND ALCOHOLS

(75) Inventors: Friedhelm Risse, Köln (DE); Pieter Ooms, Krefeld (DE); Andre Düx, Brühl (DE); Marcus Grünewald, Dortmund (DE); Thomas Pancur, Altenholz (DE); Arthur Susanto, Köln (DE); Georg Ronge, Düsseldorf (DE); Johan Vanden Eynde, Zwijnaarde (BE); Wim Wuytack, Zele (BE)

(73) Assignee: Bayer MaterialScience AG, Leverkusen (DE)

( * ) Notice: Subject to any disclaimer, the term of this patent is extended or adjusted under 35 U.S.C. 154(b) by 136 days.

(21) Appl. No.: 12/823,470

(22) Filed: Jun. 25, 2010

(65) Prior Publication Data
US 2011/0040117 A1    Feb. 17, 2011

(30) Foreign Application Priority Data

Jun. 26, 2009   (DE) .................. 10 2009 030 680

(51) Int. Cl.
*C07C 69/96*   (2006.01)
(52) U.S. Cl. ...................................... 558/277
(58) Field of Classification Search ............. 558/277
See application file for complete search history.

(56) References Cited

U.S. PATENT DOCUMENTS

| 3,642,858 | A |  | 2/1972 | Frevel et al. |
| 3,803,201 | A |  | 4/1974 | Gilpin et al. |
| 4,062,884 | A |  | 12/1977 | Romano et al. |
| 4,181,676 | A |  | 1/1980 | Buysch et al. |
| 4,307,032 | A |  | 12/1981 | Krimm et al. |
| 4,554,110 | A | * | 11/1985 | Mark ............... 558/270 |
| 4,661,609 | A |  | 4/1987 | Knifton |
| 4,691,041 | A |  | 9/1987 | Duranleau et al. |
| 4,734,519 | A |  | 3/1988 | Dunski et al. |
| 5,159,099 | A | * | 10/1992 | Romano et al. ........ 558/277 |
| 5,359,118 | A |  | 10/1994 | Wagner et al. |
| 5,847,189 | A | * | 12/1998 | Tojo et al. ............. 558/277 |
| 6,930,195 | B2 |  | 8/2005 | Buchanan et al. |

FOREIGN PATENT DOCUMENTS

| DE | 2740243 A1 | 3/1979 |
| DE | 2740251 A1 | 3/1979 |
| EP | 0001082 A1 | 3/1979 |
| EP | 0180387 A2 | 5/1986 |
| EP | 0298167 A1 | 1/1989 |
| EP | 0569812 A1 | 11/1993 |
| EP | 1086940 A1 | 3/2001 |
| EP | 1967242 A1 | 9/2008 |
| WO | WO-2007/096342 A1 | 8/2007 |
| WO | WO-2007/096343 A1 | 8/2007 |

* cited by examiner

*Primary Examiner* — Golam M M Shameem
(74) *Attorney, Agent, or Firm* — Connolly Bove Lodge & Hutz LLP

(57) ABSTRACT

The present invention relates to a continuous process for preparing lower dialkyl carbonates as main product and alkylene glycol as by-product by catalyzed transesterification of a cyclic alkylene carbonate (e.g. ethylene carbonate or propylene carbonate) with lower alcohols, where the reaction of the alkylene carbonate is carried out with an alcohol containing dialkyl carbonate in countercurrent, characterized in that introduction of a stream containing at least 99.5% by weight of alcohol takes place below the point of introduction for the alcohol containing dialkyl carbonate in a particular spacing ratio between the abovementioned points of introduction.

16 Claims, 1 Drawing Sheet

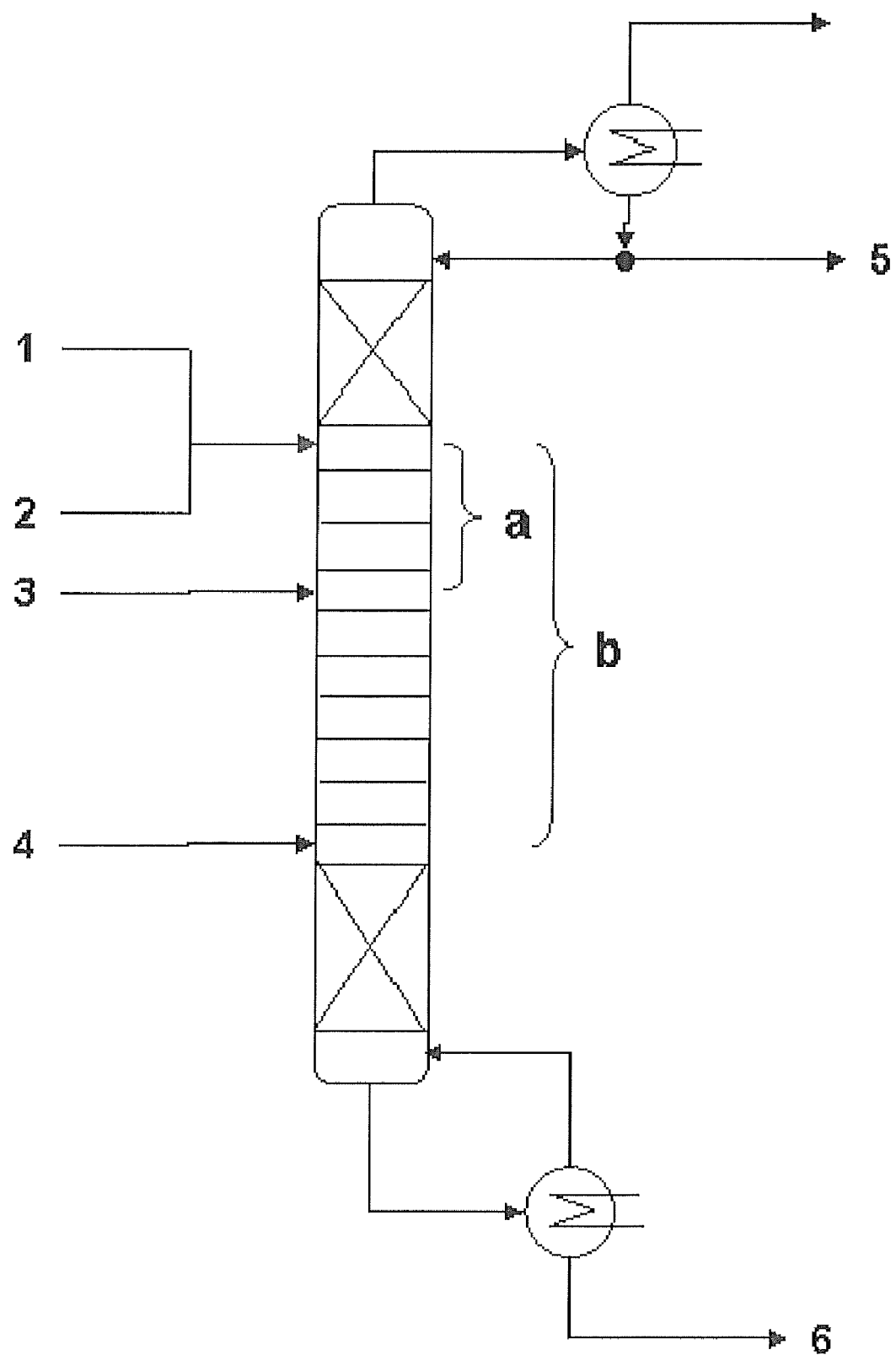

PROCESS FOR PREPARING DIALKYL CARBONATES FROM ALKYLENE CARBONATES AND ALCOHOLS

RELATED APPLICATIONS

This application claims benefit to German Patent Application No. 10 2009 030 680.3, filed Jun. 26, 2009, which is incorporated herein by reference in its entirety for all useful purposes.

BACKGROUND OF THE INVENTION

The present invention relates to a continuous process for preparing lower dialkyl carbonates as main product and alkylene glycol as by-product by catalyzed transesterification of a cyclic alkylene carbonate (e.g. ethylene carbonate or propylene carbonate) with lower alcohols, where the reaction of the alkylene carbonate is carried out with an alcohol containing dialkyl carbonate in countercurrent, characterized in that introduction of a stream containing at least 99.5% by weight of alcohol takes place below the point of introduction for the alcohol containing dialkyl carbonate in a particular spacing ratio between the abovementioned points of introduction.

The preparation of dialkyl carbonates from cyclic alkylene carbonate and alcohol, in which alkylene glycol is simultaneously formed as by-product, is known and has been widely described. In U.S. Pat. No. 6,930,195 B2, this catalyzed transesterification reaction has been described as a two-stage equilibrium reaction. In the first reaction stage, the cyclic alkylene carbonate reacts with alcohol to form hydroxyalkyl carbonate as intermediate. The intermediate is then converted by means of alcohol in the second reaction stage into the products: dialkyl carbonate and alkylene glycol. Both the quality of the by-product (alkylene glycol) and the quality of the dialkyl carbonate play a very important and decisive role for the development of an economically attractive process for preparing dialkyl carbonates. There is therefore an urgent need for a production process which can produce the alkylene glycol with a very low impurity content.

For the industrial implementation of the dialkyl carbonate production process, the use of a reactive distillation column, which has been described, inter alia, in EP 569 812 A and EP 1 086 940 A, has been found to be particularly advantageous. In EP 569 812 A, the cyclic alkylene carbonate is fed continuously into the upper part of the column and the alcohol containing dialkyl carbonate is fed continuously into the middle or lower part of the column. In addition, pure alcohol is introduced below the point of introduction of the alcohol containing dialkyl carbonate. The low boiler mixture, which comprises the dialkyl carbonate produced, is taken off continuously at the top of the column and the high boiler mixture, which comprises the alkylene glycol produced, is taken off continuously at the bottom of the column.

In EP 1 086 940, the preparation of the dialkyl carbonate was also demonstrated using a reactive distillation column. Here, the arrangement of the point of introduction of the starting material and the offtake point for the product along the reactive distillation column is similar to that in EP 569 812 except that here the additional introduction of pure alcohol in the lower region of the column has been omitted.

It has been established that the difficulties in respect of maintaining the high quality requirements for the by-product alkylene glycol can be solved particularly simply and advantageously when the content of unreacted alkylene carbonate is very small not only in the subsequent work-up steps but also immediately after the transesterification reaction.

It has been found that the impurities can be reduced only with an increased outlay (e.g. in terms of energy) by the use of the arrangement of the points of introduction of the starting materials described in EP 1 086 940. The additional use of a second point of introduction of alcohol below the point of introduction for the alcohol containing dialkyl carbonate does not on its own make maintenance of the desired purity of the products possible. In addition, this disclosed process requires the use of pure alcohol in the second point of introduction of alcohol.

There was therefore a need for a continuous process for preparing lower dialkyl carbonates as main product and alkylene glycol as by-product by catalyzed transesterification of a cyclic alkylene carbonate with lower alcohols, in which the amounts of cyclic alkylene carbonate are very low.

EMBODIMENTS OF THE INVENTION

An embodiment of the present invention is a process for continuously preparing a dialkyl carbonate of formula (I)

$$(R^1O)_2CO \quad (I)$$

wherein
$R^1$ is straight-chain or branched $C_1$-$C_4$ alkyl group, and an alkylene glycol of formula (II)

$$R^2(OH)_2 \quad (II)$$

wherein
$R^2$ is a $C_2$-$C_4$-alkyl group,
as by-product
comprising catalytically transesterifying a cyclic alkylene carbonate with an alcohol of formula (III)

$$R^1OH \quad (III)$$

wherein
$R^1$ is straight-chain or branched $C_1$-$C_4$ alkyl group,
wherein said catalyzed transesterification is carried out in countercurrent in a column, wherein (A) an cyclic alkylene carbonate (1) is introduced into the upper part of said column, (B) an alcohol (3) comprising a dialkyl carbonate is introduced into the middle or lower part of said column, (C) and a stream comprising an alcohol (4) is introduced into said column at a point on said column below the point of introduction of said alcohol (3) comprising dialkyl carbonate,
wherein the ratio of the spacing between the point of introduction of said alkylene carbonate (1) and the point of introduction of said alcohol (3) comprising a dialkyl carbonate to the spacing between the point of introduction of said alkylene carbonate (1) and the point of introduction of said stream comprising an alcohol (4) is in the range of from 0.20 to 0.52.

Another embodiment of the present invention is the above process, wherein the ratio of the spacing between the point of introduction of said alkylene carbonate (1) and the point of introduction of said alcohol (3) comprising a dialkyl carbonate to the spacing between the point of introduction of said alkylene carbonate (1) and the point of introduction of said stream comprising an alcohol (4) is in the range of from 0.28 to 0.44.

Another embodiment of the present invention is the above process, wherein the dialkyl carbonate content of said alcohol (3) comprising a dialkyl carbonate is in the range of from 0.2 to 30% by weight.

Another embodiment of the present invention is the above process, wherein said cyclic alkylene carbonate is ethylene carbonate or propylene carbonate.

Another embodiment of the present invention is the above process, wherein said alcohol is methanol and said dialkyl carbonate is dimethyl carbonate.

Another embodiment of the present invention is the above process, wherein the proportion by weight of said cyclic alkylene carbonate in said high boiler stream is maintained below 1000 ppm.

Another embodiment of the present invention is the above process, wherein the proportion by weight of said cyclic alkylene carbonate in said high boiler stream is maintained below 500 ppm Another embodiment of the present invention is the above process, wherein said stream comprising an alcohol (4) is an alcohol having a purity of at least 90% by weight.

Another embodiment of the present invention is the above process, wherein said stream comprising an alcohol (4) is an alcohol having a purity of at least 95% by weight.

Another embodiment of the present invention is the above process, wherein said stream comprising an alcohol (4) is an alcohol having a purity of at least 99.5% by weight.

Another embodiment of the present invention is the above process, wherein said catalyzed transesterification is carried out in the presence of a homogeneous catalyst.

Another embodiment of the present invention is the above process, wherein potassium hydroxide or sodium hydroxide is used as the catalyst in said catalyzed transesterification.

Another embodiment of the present invention is the above process, wherein said column comprises at least one enrichment section in the upper part of said column and at least one reaction zone below said at least one enrichment section.

Another embodiment of the present invention is the above process, wherein said column comprises at least one stripping section below a reaction zone.

Another embodiment of the present invention is the above process, wherein said column comprises at least one reaction zone, wherein the temperature of said at least one reaction zone is in the range from 20 to 200° C. and the pressure at the top of said column is in the range from 0.4 to 5 bar.

Another embodiment of the present invention is the above process, wherein said cyclic alkylene carbonate compound and said alcohol are used in a molar ratio of from 1:2.0 to 1:20.

BRIEF DESCRIPTION OF THE DRAWING

FIG. 1 schematically depicts a transesterification column into which the three feed streams, i.e. a stream 1 containing the cyclic alkylene carbonate, stream 3 containing the alcohol and smaller amounts of the dialkyl carbonate and stream 4 containing a higher concentration of alcohol, are fed in the region of a reaction zone RZ in the form of a countercurrent esterification and reacted to form dialkyl carbonates and alkylene glycols.

DESCRIPTION OF THE INVENTION

This object has surprisingly been achieved by the ratio of the spacing between the point of introduction of alkylene carbonate and the first point of introduction of alcohol (see FIG. 1, spacing a) to the spacing between the point of introduction of alkylene carbonate and the second point of introduction of alcohol (FIG. 1, spacing b) being from 0.2 to 0.52, preferably from 0.25 to 0.48, particularly preferably from 0.28 to 0.44.

In the process of the invention, an alcohol containing dialkyl carbonate and having a dialkyl carbonate content of preferably from 0.2 to 30% by weight is used for the first point of introduction of alcohol.

The invention accordingly provides a process for the continuous preparation of dialkyl carbonate of the formula $$(R^1O)_2CO \tag{I}$$

where $R^1$ is straight-chain or branched $C_1$-$C_4$, and of alkylene glycol of the formula

where $R^2$ is ethyl or propyl, as by-product by catalyzed transesterification of cyclic ethylene carbonate or propylene carbonate with an alcohol of the formula $$R^1OH \tag{III}$$

where $R^1$ is as defined above, characterized in that the transesterification is carried out in countercurrent in a column with ethylene carbonate or propylene carbonate (1) being introduced into the upper part of the column and an alcohol (3) containing dialkyl carbonate and having a dialkyl carbonate content of preferably from 0.2 to 30% by weight being introduced into the middle or lower part of the column and a further point of introduction for an alcohol-containing stream (4) being additionally provided below the point of introduction of the alcohol containing dialkyl carbonate, where the ratio of the spacing between the point of introduction containing alkylene carbonate (1) and the point of introduction of the alcohol (3) containing dialkyl carbonate to the spacing between the point of introduction of alkylene carbonate (1) and the second point of introduction of alcohol (4) is from 0.20 to 0.52.

In the process of the invention, adherence to the spacing ratio mentioned surprisingly makes it unnecessary to use pure alcohol in the second, lowermost point of introduction of alcohol. Here, the use of an alcohol having a purity of at least 90% by weight, preferably at least 95% by weight and particularly preferably at least 99.5% by weight, is entirely sufficient. An alcohol having a purity of up to 99.99% by weight is preferably used.

Preference is given to proportions by weight of cyclic alkylene carbonate of less than 1000 ppm, particularly preferably less than 500 ppm, in the high boiler mixture which is continuously taken off at the bottom of the column.

Dialkyl carbonates prepared according to the invention are preferably those of the general formula (IV)

where $R^1$ and $R^2$ are each, independently of one another, linear or branched, optionally substituted $C_1$-$C_{34}$-alkyl, preferably $C_1$-$C_6$-alkyl, particularly preferably $C_1$-$C_4$-alkyl. $R^1$ and $R^2$ can be identical or different. Preference is given to $R^1$ and $R^2$ being identical.

For the purposes of the invention, $C_1$-$C_4$-alkyl is, for example, methyl, ethyl, n-propyl, isopropyl, n-butyl, sec-butyl, tert-butyl, $C_1$-$C_6$-alkyl also, for example, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl or 1-ethyl-2-methylpropyl, $C_1$-$C_{34}$-alkyl also, for example, n-heptyl and n-octyl, pinacyl, adamantyl, the isomeric menthyls, n-nonyl, n-decyl, n-dodecyl, n-tridecyl, n-tetradecyl, n-hexadecyl or n-octadecyl. The same applies to the corresponding alkyl radical in, for example, aralkyl or alkylaryl radicals. Alkylene radicals in the corresponding hydroxyalkyl or aralkyl or alkylaryl radicals are, for example, the alkylene radicals corresponding to the above alkyl radicals.

The above listings are to be understood as being by way of example and not constituting a limitation.

Preferred dialkyl carbonates are dimethyl carbonate, diethyl carbonate, di(n-propyl)carbonate, di(iso-propyl)carbonate, di(n-butyl)carbonate, di(sec-butyl)carbonate, di(tert-butyl)carbonate and dihexyl carbonate. Particular preferences is given to dimethyl carbonate and diethyl carbonate. Very particular preference is given to dimethyl carbonate.

Cyclic alkylene carbonates used for the purposes of the invention are preferably those having the formula (V):

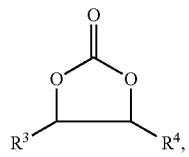

(V)

where, in the formula, $R^3$ and $R^4$ are each, independently of one another, hydrogen, substituted or unsubstituted $C_1$-$C_4$-alkyl, substituted or unsubstituted $C_2$-$C_4$-alkenyl or substituted or unsubstituted $C_6$-$C_{12}$-aryl and $R^3$ and $R^4$ together with the two three-ring carbon atoms can form a saturated carbocyclic ring having 5-8 ring atoms.

The cyclic alkylene carbonates are reacted with alcohols of the formula $R^5$—OH where $R^5$ is a straight-chain or branched $C_1$-$C_4$-alkyl.

The transesterification catalysts which can be used according to the invention are those known to a person skilled in the art, for example hydrides, oxides, hydroxides, alkoxides, amides or salts of alkali metals such as lithium, sodium, potassium, rubidium and caesium, preferably of lithium, sodium and potassium, particularly preferably of sodium and potassium (U.S. Pat. No. 3,642,858 A, U.S. Pat. No. 3,803, 201 A, EP 1 082 A). If alkoxides are used, these can, according to the invention, also be formed in situ by use of the elemental alkali metals and the alcohol to be reacted according to the invention. Salts of alkali metals can be those of organic or inorganic acids, e.g. of acetic acid, propionic acid, butyric acid, benzoic acid, stearic acid, carbonic acid (carbonates or hydrogencarbonates), of hydrochloric acid, hydrobromic acid or hydroiodic acid, nitric acid, sulphuric acid, hydrofluoric acid, phosphoric acid, hydrocyanic acid, thiocyanic acid, boric acid, stannic acid, $C_1$-$C_4$-stannonic acids or antimonic acids. As compounds of alkali metals, preference is given to the oxides, hydroxides, alkoxides, acetates, propionates, benzoates, carbonates and hydrogencarbonates, with particular preference being given to using hydroxides, alkoxides, acetates, benzoates or carbonates. Such alkali metal compounds (if appropriate formed in situ from the free alkali metals) are used in amounts of from 0.001 to 2% by weight, preferably from 0.003 to 1.0% by weight, particularly preferably from 0.005 to 1.0% by weight, based on the reaction mixture to be reacted.

According to the invention, it is possible, if appropriate, to add complexing substances to such alkali metal compounds. Examples which may be mentioned are crown ethers such as dibenzo-18-crown-6, polyethylene glycols or bicyclic nitrogen-containing cryptands.

Such complexing agents are used in amounts of from 0.1 to 200 mol %, preferably from 1 to 100 mol %, based on the alkali metal compound.

Further suitable catalysts for the process of the invention are thallium(I) and thallium(lll) compounds such as the oxides, hydroxides, carbonates, acetates, bromides, chlorides, fluorides, formates, nitrates, cyanates, stearates, naphthenates, benzoates, cyclohexylphosphonates, hexahydrobenzoates, cyclopentandienylthallium, thallium methoxide, thallium ethoxide, preferably Tl(I) oxide, Tl(I) hydroxide, Tl(I) carbonate, Tl(I) acetate, Tl(III) acetate, Tl(I) fluoride, Tl(I) formate, Tl(I) nitrate, Tl(I) naphthenate and Tl-(I) methoxide (EP 1 083). The amounts of thallium catalyst are not particularly critical. They are generally 0.0001-10% by weight, preferably 0.001-1% by weight, based on the total reaction mixture. Nitrogen-containing bases can also be used as catalysts (U.S. Pat. No. 4,062,884) in the process of the invention. Mention may be made by way of example of secondary or tertiary amines such as triethylamine, tributylamine, methyldibenzylamine, dimethylcyclohexylamine, etc.

The amounts used according to the invention of the nitrogen-containing bases are from 0.01 to 10% by weight, preferably from 0.1 to 5% by weight, particularly preferably from 0.1 to 1% by weight, based on the total reaction mixture. According to the invention, compounds from the group consisting of phosphines, stibines, arsines and divalent sulphur and selenium compounds and also their onium salts can also be used as catalysts (EP 180 387, U.S. Pat. No. 4,734,519).

Mention may be made by way of example of the following: tributylphosphine, triphenylphosphine, diphenylphosphine, 1,3-bis(diphenylphosphino)propane, triphenylarsine, trimethylarsine, tributylarsine, 1,2-bis(diphenylarsino)ethane, triphenylantimony, diphenyl sulphide, diphenyl disulphide, diphenyl selenide, tetraphenylphosphonium halide (Cl, Br, I), tetraphenylarsonium halide (Cl, Br, I), triphenylsulphonium halide (Cl, Br), etc.

The amounts used according to the invention in the case of this group of catalysts are in the range from 0.1 to 10% by weight, preferably from 0.1 to 5% by weight, particularly preferably in the range from 0.1 to 2% by weight, based on the total reaction mixture.

Furthermore, complexes or salts of tin, titanium or zirconium (U.S. Pat. No. 4,661,609) can be used according to the invention. Examples of such systems are butylstannonic acid, tin methoxide, dimethyltin, dibutyltin oxide, dibutyltin dilaurate, tributyltin hydride, tributyltin chloride, tin(II) ethylhexanoate, zirconium alkoxides (methyl, ethyl, butyl), zirconium (IV) halides (F, Cl, Br, I), zirconium nitrates, zirconium acetylacetonate, titanium alkoxides (methyl, ethyl, isopropyl), titanium acetate, titanium acetylacetonate, etc.

The amounts which can be used according to the invention are from 0.1 to 10% by weight, preferably from 0.1 to 5% by weight, based on the total mixture.

It is also possible to use bifunctional catalysts of the formula (VI)

$$[A_aX_b]_m\cdot[B_cY_d]_n \qquad (VI)$$

in the process of the invention. In these bifunctional catalysts, the molar ratio of the two components in square brackets is expressed by the indices m and n. These indices can, independently of one another, assume values of 0.001-1, preferably 0.01-1, particularly preferably 0.05-1 and very particularly preferably 0.1-1. Within the square brackets are uncharged salts in each case composed of a cation and an anion. The indices a and b are, independently of one another, integers of 1-5; the indices c and d are, independently of one another, integers of 1-3, matching the requirements of the valencies of the cations and anions to form such uncharged salts. Furthermore, in (VI), A is the cation of a metal belonging to the third period and group IIa, the fourth period and group IIa, IVa-VIIIa, Ib or IIb, the fifth period and group IIa, IVa-VIIa or IVb or the sixth period and group IIa-VIa of the Periodic Table of the Elements in the short period form.

Possible metals for the cation A are taken by a person skilled in the art from the usual depictions of the Periodic Table of the Elements (Mendeleev) in the short period form. A is preferably the cation of one of the metals Mg, Ca, Sr, Ba, Zn, Cu, Mn, Co, Ni, Fe, Cr, Mo, W, Ti, Zr, Sn, Hf, V and Ta, preferably the cation of one of the metals Mg, Ca, Zn, Co, Ni, Mn, Cu and Sn. Apart from the uncomplexed cations of the metals mentioned, cationic oxo complexes of the metals mentioned are also possible, for example titanyl $TiO^{++}$ and chromyl $CrO_2^{++}$.

The anion X associated with the cation A is that of an inorganic or organic acid. Such an inorganic or organic acid can be monobasic or dibasic or tribasic. Such acids and their anions are known to those skilled in the art. Examples of anions of monobasic inorganic or organic acids are: fluoride, bromide, chloride, iodide, nitrate, the anion of an alkanecarboxylic acid having 1-18 carbon atoms and benzoate; examples of anions of dibasic inorganic or organic acids are: sulphate, oxalate, succinate, fumarate, maleate, phthalate and others; examples of tribasic inorganic or organic anions are: phosphate and citrate. Preferred anions X in the catalyst of the formula (VI) are: fluoride, chloride, bromide, iodide, sulphate, nitrate, phosphate, formate, acetate, propionate, oxalate, butyrate, citrate, succinate, fumarate, maleate, benzoate, phthalate, decanoate, stearate, palmitate and laurate. Particularly preferred anions X are: chloride, bromide, iodide, acetate, laurate, stearate, palmitate, decanoate, nitrate and sulphate.

As cation B in the catalyst of the formula (VI), it is possible to use a cation from the group consisting of alkali or alkaline earth metal cations, quaternary ammonium, phosphonium, arsonium or stibonium cations and ternary sulphonium cations.

As alkali or alkaline earth metal cations, mention may here be made of: the lithium, sodium, potassium, rubidium, caesium, magnesium, calcium, strontium and barium cations, preferably the alkali metal cations mentioned, particularly preferably the sodium cation and the potassium cation.

As cations B, preference is given to those of the formula (VII)

(VII)

where
$Q^1$ is N, P, As or Sb and
$R^6$, $R^7$, $R^8$ and $R^9$ are each, independently of one another, straight-chain or branched $C_1$-$C_{18}$ or $C_7$-$C_{12}$-aralkyl and one of the radicals $R^6$-$R^9$ can also be. B is particularly preferably a cation of the formula (VIII)

(VIII)

where,
$Q^2$ is N or P, preferably N.
In the formulae (VII) and (VIII), the radicals $R^6$, $R^7$, $R^8$ and $R^9$ are very particularly preferably replaced by the radicals $R^{16}$, $R^{17}$, $R^{18}$ and $R^{19}$ which are each, independently of one another, straight-chain or branched $C_1$-$C_{18}$-alkyl or $C_7$-$C_8$-aralkyl and one of the radicals $R^{16}$ to $R^{19}$ can also be phenyl. The radicals $R^{16}$, $R^{17}$, $R^{18}$ and $R^{19}$ are very particularly preferably replaced by the radicals $R^{26}$, $R^{27}$, $R^{28}$ and $R^{29}$ which are each, independently of one another, $C_1$-$C_8$-alkyl or benzyl and one of the radicals $R^{26}$ to $R^{29}$ can also be phenyl.

Straight-chain or branched $C_1$-$C_{18}$-alkyl is, for example, methyl, ethyl, propyl, isopropyl, butyl, isobutyl, hexyl, octyl, dodecyl, hexadecyl or octadecyl. Preferred alkyl has 1-12 carbon atoms, and particularly preferred alkyl has 1-8 carbon atoms.

$C_7$-$C_{12}$-Aralkyl is, for example, benzyl, phenylethyl, phenylpropyl, naphthylmethyl or naphthylethyl; a preferred aralkyl is benzyl or phenylethyl, very particularly preferably benzyl.

$C_6$-$C_{12}$-Aryl is, for example, phenyl, naphthyl or biphenylyl, preferably phenyl.

The anion Y in the catalyst of the formula (VI) is a halide ion such as fluoride, chloride, bromide or iodide, preferably bromide or iodide, particularly preferably iodide. However, it can also have the meaning of other anions mentioned under X if in the specific case the anion X is bromide or iodide.

The bifunctional catalyst of the formula (VI) is used in an amount of 0.005-5% by weight, preferably 0.01-3% by weight, particularly preferably 0.01-1% by weight, based on the total transesterification mixture.

These amounts of catalyst partly differ from the amounts mentioned in the literature. It is particularly surprising that relatively high concentrations of the effective catalysts based on alkali metal compounds can be used in the process of the invention without evolution of $CO_2$, which would reduce the yield and hinder the carrying out of the reaction, and formation of polyols, as is known, for example, from DE-A 2 740 243 and the literature cited therein and from DE-A 2 740 251, occurring. This, too, is a surprising aspect of the process of the invention.

Such catalysts can be introduced in homogeneously dissolved form at the top of the column, with alkylene carbonate, alkylene glycol, alcohol or diallyl carbonate, i.e. solvents intrinsic to the system, being employed as solvents. It is of course also possible to use insoluble transesterification catalysts which are arranged on intermediate trays or in the middle of packing elements. In such a case, introduction of a dissolved catalyst via (2) can be omitted. Suitable heterogeneous catalysts are, for example:

Ion-exchange resins having functional groups selected from among tertiary amines, quaternary ammonium groups, with hydroxide, chloride or hydrogen sulphates being mentioned by way of example as counterions, sulphonic acid groups or carboxyl groups, with hydrogen, alkali metals or alkaline earth metals being mentioned by way of example as counterions for both. These functional groups can be bound either directly or via inert chains to the polymer (U.S. Pat. No. 4,062,884 A, U.S. Pat. No. 4,691,041 A, EP 298 167 A). Mention may also be made of alkali metal or alkaline earth metal silicates impregnated on silicon dioxide supports, and also ammonium-exchanged zeolites.

The process of the invention can be carried out continuously or batchwise. Preference is given to a continuous process.

In the process of the invention, the cyclic alkylene carbonate compound(s) and the alcohol(s) are preferably used in a molar ratio of from 1:0.1 to 1:40, particularly preferably from 1:1.0 to 1:30, very particularly preferably from 1:2.0 to 1:20. The molar ratio indicated does not take into account the recirculation of cyclic alkylene carbonate compound or alcohol into the transesterification column via one or more condenser(s) at the top (cf. under (b)) or one or more bottom vaporizer(s) which may be present.

The catalyst is preferably introduced into the transesterification column together with the stream containing the cyclic alkylene carbonate in dissolved or suspended form via a point of introduction which is arranged above the point of introduction of the alcohol. As an alternative, the catalyst can also be introduced separately, for example as a solution in the alcohol, in the alkylene glycol or in a suitable inert solvent. If heterogeneous catalysts are used, these can be used in admixture with the abovementioned packing elements, in suitable form instead of packing elements or as a bed on any built-in column trays.

The process of the invention is carried out in a transesterification column. In preferred embodiments of the process of the invention, the liquid stream taken off at the bottom of this transesterification column can, if appropriate after being concentrated, be subjected to further reaction and/or purification in one or more further steps. Individual steps among such further steps or all such further steps can preferably be carried out in one or more further columns.

Possible transesterification columns or, if appropriate, second or further column(s) are the columns known to those skilled in the art. These are, for example, distillation or rectification columns, preferably reactive distillation or reactive rectification columns.

The transesterification column preferably contains at least one enrichment section in the upper part of the column and at least one reaction zone below the enrichment section. Preference is given to each of the two sections independently having from 0 to 30, preferably from 0.1 to 30, theoretical plates.

In preferred embodiments, the transesterification column has at least one stripping section below a reaction zone.

Furthermore, the transesterification column can preferably be equipped with one or more bottom vaporizer(s). When the transesterification column has a stripping section, preference is given to using an additional bottom vaporizer which completely or partly vaporizes the liquid flowing down from the stripping section. This completely or partly vaporized liquid stream is recirculated in its entirety or in part to the transesterification column. In the case of an embodiment without a stripping section, the liquid running down from the reaction zone is completely or partly vaporized, if appropriate, in a bottom vaporizer which may be used and recirculated completely or partly to the transesterification column.

The enrichment section(s) can, in preferred embodiments, be accommodated together with the reaction section(s) and, if appropriate, at least one stripping section in the transesterification column. Here, the gaseous mixture travelling upwards from the reaction zone(s) is introduced into a lower section of the enrichment section or, if appropriate, the lower enrichment section, with depletion in the alkylene carbonate or alkylene glycol taking place.

Below the reaction zone and any stripping section present, a mixture containing alkylene glycol, excess or unreacted alkylene carbonate, alcohol, dialkyl carbonate, transesterification catalysts and high-boiling compounds which are formed in the reaction or were originally present in the starting materials is obtained. When a stripping section is used, the content of low-boiling compounds, for example dialkyl carbonate and alcohol, is reduced, with further dialkyl carbonate and alkylene glycol sometimes being formed in the presence of the transesterification catalyst. The energy required for this is preferably supplied by one or more vaporizers.

In all sections of the transesterification column, i.e. both in the enrichment section and any stripping section and also in the reaction zone, it is possible to use random packing elements or ordered packing. The random packing elements or ordered packing to be used are those customary for distillations, as are described, for example, in Ullmann's Encyclopädie der Technischen Chemie, 4th edition, vol. 2, p. 528 ff. Examples of random packing elements are Raschig or Pall and Novalox rings, Berl, Intalex or Torus saddles, Interpack bodies and examples of ordered packings are sheet metal and mesh packings (e.g. BX packings, Montz Pak, Mellapak, Melladur, Kerapak and CY packing) made of various materials such as glass, stoneware, porcelain, stainless steel, plastic. Preference is given to random packing elements and ordered packings which have a large surface area, can be wetted readily and have a sufficient residence time of the liquid phase. These are, for example, Pall and Novolax rings, Berl saddles, BX packings, Montz Pak, Mellpak, Melladur, Kerapak and CY packings.

As an alternative, column trays such as sieve trays, bubble-cap trays, valve trays and tunnel trays are also suitable. In the reaction zone(s) of the transesterification column, column trays having long residence times with good mass transfer, for example bubblecap trays, valve trays or tunnel trays with high overflow weirs, are particularly preferred. The number of theoretical plates in the reaction zone is preferably from 3 to 50, particularly preferably from 10 to 50 and very particularly preferably from 10 to 40. The liquid hold-up is preferably from 1 to 80%, particularly preferably from 5 to 70% and very particularly preferably from 7 to 60%, of the interior column volume of the reaction zone. The more precise design of the reaction zone(s), any stripping section to be used and the enrichment section(s) can be carried out by a person skilled in the art.

The temperature of the reaction zone(s) is preferably in the range from 20 to 200° C., particularly preferably from 40 to 180° C., very particularly preferably from 50 to 160° C. It is advantageous to carry out the transesterification according to the invention not only at atmospheric pressure but also at elevated or reduced pressure. The pressure of the reaction zone is therefore preferably in the range from 0.2 to 20 bar, particularly preferably from 0.3 to 10 bar, very particularly preferably from 0.4 to 5 bar. In the pressures indicated above and below are, unless explicitly stated otherwise, absolute pressures.

The process of the invention is shown schematically by way of example in FIG. 1. In the FIGURE, the reference symbols have the following meanings:

1: stream containing cyclic alkylene carbonate
2: stream containing the catalyst as a suspension or as a solution in a substance intrinsic to the system (when a homogeneous catalyst is used in the process); substances intrinsic to the system are: alkylene carbonate, alcohol, dialkyl carbonate and alkylene glycol
3: stream containing alcohol and small proportions of dialkyl carbonate
4: stream containing alcohol
5: low boiler stream containing, inter alia, dialkyl carbonate and alcohol
6: high boiler stream containing, inter alia, alkylene glycol, alkylene carbonate, alcohol, high boilers and traces of further by-products and, if appropriate, catalyst
a: spacing between point of introduction of the alkylene carbonate and stream 3
b: spacing between point of introduction of the alkylene carbonate and stream 4

FIG. 1 shows a transesterification column into which the three feed streams, i.e. a stream 1 containing the cyclic alkylene carbonate, stream 3 containing the alcohol and smaller amounts of the dialkyl carbonate and stream 4 containing a higher concentration of alcohol, are fed in the region of a reaction zone RZ in the form of a countercurrent esterification and reacted to form dialkyl carbonates and alkylene glycols.

Streams 3 and 4 are conveyed in countercurrent to stream 1. Stream 1 is fed in liquid form into the transesterification column, while streams 3 and 4 are fed in gaseous form and, if appropriate, slightly superheated into the column. Depending on the source of the starting materials used, these correspondingly contain typical impurities. Stream 3 contains alcohol as main component and, for example, from 0 to 40% by weight, preferably 0.1-35% by weight and particularly preferably 0.2-30% by weight, of the dialkyl carbonate. Further components of stream 3 have a total proportion of <1% by weight. Stream 4, on the other hand, has a proportion of >90% by weight, preferably >95% by weight and particularly preferably >99% by weight, of alcohol.

The molar ratio of the alkylene carbonate fed to the column via stream 1 to the total amount of the alcohol fed in via streams 3 and 4 is from 1:0.1 to 1:40, particularly preferably from 1:1.0 to 1:30, very particularly preferably from 1:2.0 to 1:20. The total amount of the alcohol fed in via streams 3 and 4 is divided between stream 4 and stream 3 in a ratio of stream 4:stream 3 of from 1:1 to 1:15, preferably from 1:1.2 to 1:12, particularly preferably from 1:1.4 to 1:8.

The molar ratio of the catalyst fed into the column via stream 2 to stream 1 of the alkylene carbonate is from 0.01 to 2 mol %, preferably from 0.02 to 1.8 mol %, particularly preferably from 0.03 to 1.6 mol %.

The column in FIG. 1 comprises an enrichment section located above the reaction zone, the reaction zone itself and the stripping section located below the reaction zone. The geometric definition of the reaction zone is fixed by two elements, namely the uppermost point of introduction of the alkylene carbonate (stream 1) and the bottommost point of introduction of the alcohol (stream 4). The reaction of alkylene carbonate and alcohol to form dialkyl carbonate and alkylene glycol is a two-stage equilibrium reaction (see, for example, U.S. Pat. No. 6,930,195 B2). Both the forward and backward reactions are not restricted to the reaction zone.

The following examples serve to illustrate the invention by way of example and are not to be construed as a restriction.

All the references described above are incorporated by reference in their entireties for all useful purposes.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

EXAMPLES

Example 1

A reactive distillation column comprising an enrichment section having 9 theoretical plates, a reaction zone having 25 reaction trays (holdup/tray: 0.6 m$^3$) and a stripping section having 4 theoretical plates is operated at a pressure measured at the top of the column of 400 mbar (absolute) and a reflux ratio of 0.66.

9000 kg/h of ethylene carbonate and 58 kg/h of a mixture of 33.3% by weight of KOH and 66.7% by weight of ethylene glycol are fed continuously into the upper column region directly above the first reaction tray. Between the 8$^{th}$ and 9$^{th}$ reaction trays, 21 437 kg/h of a gaseous mixture of 83.7% by weight of methanol and 16.3% by weight of dimethyl carbonate are fed in. In addition, 7146 kg/h of a gaseous mixture of 99.5% by weight of methanol, 0.45% by weight of ethylene glycol and 500 ppm of dimethyl carbonate are fed in at the lower end of the reaction zone. This corresponds to a spacing ratio a/b of 0.36.

A partial condenser condenses the vapour stream at the top of the column at 40° C. 6 kg/h of gaseous distillate and also 30 729 kg/h of liquid distillate having a composition of 59% by weight of methanol and 41% by weight of dimethyl carbonate, which is passed to further purification steps, are obtained.

The bottom vaporizer is operated at 102° C., and 7022 kg/h of liquid bottom product comprising mainly ethylene glycol and, inter alia, 400 ppm of ethylene carbonate are obtained.

Comparative Example 1

The same reactive distillation column as described in Example 1 is used. The column is operated at a pressure measured at the top of the column of 400 mbar (absolute) and a reflux ratio of 0.66.

9000 kg/h of ethylene carbonate and 58 kg/h of a mixture of 33.3% by weight of KOH and 66.7% by weight of ethylene glycol are fed continuously into the upper column region directly above the first reaction tray. Between the 14th and 15th reaction trays, 21 437 kg/h of a gaseous mixture of 83.7% by weight of methanol and 16.3% by weight of dimethyl carbonate are fed in. In addition, 7146 kg/h of a gaseous mixture of 99.5% by weight of methanol, 0.45% by weight of ethylene glycol and 500 ppm of dimethyl carbonate are fed in at the lower end of the reaction zone. This corresponds to a spacing ratio a/b of 0.6. The ratio of the total methanol fed in and the ethylene carbonate remains the same as in Example 1.

A partial condenser condenses the vapour stream at the top of the column at 40° C. 6 kg/h of gaseous distillate and also 30 727 kg/h of liquid distillate having a composition of 59% by weight of methanol and 41% by weight of dimethyl carbonate, which is passed to further purification steps, are obtained.

The bottom vaporizer is operated at 102° C., and 7024 kg/h of liquid bottom product comprising mainly ethylene glycol and, inter alia, 1100 ppm of ethylene carbonate are obtained.

Comparative Example 2

The same reactive distillation column as described in Example 1 is used. The column is operated at a pressure measured at the top of the column of 400 mbar (absolute) and a reflux ratio of 0.66.

9000 kg/h of ethylene carbonate and 58 kg/h of a mixture of 33.3% by weight of KOH and 66.7% by weight of ethylene glycol are fed continuously into the upper column region directly above the first reaction tray. Between the 10$^{th}$ and 11$^{th}$ reaction trays, 25 830 kg/h of a gaseous mixture of 97% by weight of methanol and 3% by weight of dimethyl carbonate are fed in. A further point of introduction for methanol was omitted. The ratio of the total methanol fed in and the ethylene carbonate remains the same as in Example 1.

A partial condenser condenses the vapour stream at the top of the column at 40° C. 6 kg/h of gaseous distillate and also 27 998 kg/h of liquid distillate having a composition of 64% by weight of methanol and 36% by weight of dimethyl carbonate, which is passed to further purification steps, are obtained.

The bottom vaporizer is operated at 102° C., and 7002 kg/h of liquid bottom product comprising mainly ethylene glycol and, inter alia, 5000 ppm of ethylene carbonate are obtained.

Comparative Example 3

The same reactive distillation column as described in Example 1 is used. The column is operated at a pressure measured at the top of the column of 400 mbar (absolute) and a reflux ratio of 0.66.

9000 kg/h of ethylene carbonate and 58 kg/h of a mixture of 33.3% by weight of KOH and 66.7% by weight of ethylene glycol are fed continuously into the upper column region directly above the first reaction tray. Between the 19$^{th}$ and 20$^{th}$ reaction trays, 29 935 kg/h of a gaseous mixture of 83.7% by weight of methanol and 16.3% by weight of dimethyl carbonate are fed in. A further point of introduction for methanol was omitted. The ratio of the total methanol fed in and the ethylene carbonate remains the same as in Example 1.

A partial condenser condenses the vapour stream at the top of the column at 40° C. 6 kg/h of gaseous distillate and also 31 938 kg/h of liquid distillate having a composition of 57.4% by weight of methanol and 42.6% by weight of dimethyl carbonate, which is passed to further purification steps, are obtained.

The bottom vaporizer is operated at 102° C., and 71.66 kg/h of liquid bottom product comprising mainly ethylene glycol and, inter alia, 5.3% by weight of ethylene carbonate are obtained.

The invention claimed is:

1. A process for continuously preparing a dialkyl carbonate of formula (I)

$$(R^1O)_2CO \quad (I)$$

wherein
R$^1$ is straight-chain or branched C$_1$-C$_4$ alkyl group,
and
an alkylene glycol of formula (II)

$$R^2(OH)_2 \quad (II)$$

wherein
R$^2$ is a C$_2$-C$_4$-alkyl group,
as by-product
comprising reacting
a cyclic alkylene carbonate having the following formula:

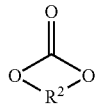

wherein
R$^2$ is a C$_2$-C$_4$-alkyl group,
with
an alcohol of formula (III)

$$R^1OH \quad (III)$$

wherein
R$^1$ is straight-chain or branched C$_1$-C$_4$ alkyl group,
in the presence of a catalyst,
wherein said reaction is carried out in countercurrent in a column, wherein said reaction comprises the steps of
(A) introducing said cyclic alkylene carbonate as a stream into the upper part of said column at point (1),
(B) introducing said alcohol of formula (III), which comprises said dialkyl carbonate of formula (I), as a stream into the middle or lower part of said column at point (3), and
(C) introducing a stream comprising said alcohol of formula (III) as a stream into said column at a point (4) on said column below point (3),
wherein the ratio of the spacing between point (1) and point (3) to the spacing between point (1) and point (4) is in the range of from 0.20 to 0.52.

2. The process of claim 1, wherein the ratio of the spacing between point (1) and point (3) to the spacing between point (1) and point (4) is in the range of from 0.28 to 0.44.

3. The process of claim 1, wherein the dialkyl carbonate of formula (I) content of said alcohol of formula (III) comprising said dialkyl carbonate of formula (I) is in the range of from 0.2 to 30% by weight.

4. The process of claim 1, wherein said cyclic alkylene carbonate is ethylene carbonate or propylene carbonate.

5. The process of claim 1, wherein said alcohol of formula (III) is methanol and said dialkyl carbonate of formula (I) is dimethyl carbonate.

6. The process of claim 1, wherein the proportion by weight of said cyclic alkylene carbonate in said stream is maintained below 1000 ppm.

7. The process of claim 1, wherein the proportion by weight of said cyclic alkylene carbonate in said stream is maintained below 500 ppm.

8. The process of claim 1, wherein said stream introduced at point (4) is an alcohol having a purity of at least 90% by weight.

9. The process of claim 1, wherein said stream introduced at point (4) is an alcohol having a purity of at least 95% by weight.

10. The process of claim 1, wherein said stream introduced at point (4) is an alcohol having a purity of at least 99.5% by weight.

11. The process of claim 1, wherein said catalyst is a homogeneous catalyst.

12. The process of claim 1, wherein said catalyst is potassium hydroxide or sodium hydroxide.

13. The process of claim 1, wherein said column comprises at least one enrichment section in the upper part of said column and at least one reaction zone below said at least one enrichment section.

14. The process of claim 1, wherein said column comprises at least one stripping section below a reaction zone.

15. The process of claim 1, wherein said column comprises at least one reaction zone, wherein the temperature of said at least one reaction zone is in the range from 20 to 200° C. and the pressure at the top of said column is in the range from 0.4 to 5 bar.

16. The process of claim 1, wherein said cyclic alkylene carbonate and said alcohol of formula (III) are used in a molar ratio of from 1:2.0 to 1:20.

* * * * *